United States Patent
Ingrisch et al.

(10) Patent No.: US 7,745,565 B2
(45) Date of Patent: Jun. 29, 2010

(54) AZETIDINE DERIVATIVES, METHOD FOR PRODUCING SAID DERIVATIVES AND USE THEREOF

(75) Inventors: Stefan Ingrisch, Seebruck (DE); Alois Maier, Engelsberg (DE); Thomas Pfeuffer, Trostberg (DE); Norbert Steidl, Kienberg (DE); Herbert Winkelmann, Garching (DE); Andrea Gantner, legal representative, Garching (DE)

(73) Assignee: Construction Research & Technology GmbH, Trostberg (DE)

( * ) Notice: Subject to any disclaimer, the term of this patent is extended or adjusted under 35 U.S.C. 154(b) by 679 days.

(21) Appl. No.: 10/581,624

(22) PCT Filed: Dec. 2, 2004

(86) PCT No.: PCT/EP2004/013730

§ 371 (c)(1),
(2), (4) Date: Apr. 17, 2007

(87) PCT Pub. No.: WO2005/054185

PCT Pub. Date: Jun. 16, 2005

(65) Prior Publication Data

US 2008/0045690 A1    Feb. 21, 2008

(30) Foreign Application Priority Data

Dec. 3, 2003   (DE) ................. 103 56 489

(51) Int. Cl.
 C07D 205/04  (2006.01)
(52) U.S. Cl. .............. 528/364; 528/408; 548/950; 548/952; 525/329.9; 525/375
(58) Field of Classification Search ........... 548/952, 548/950; 525/329.9, 375; 528/368, 408
See application file for complete search history.

(56) References Cited

U.S. PATENT DOCUMENTS 4,576,980 A    3/1986  Dai et al.
4,880,869 A    11/1989 Aoki et al.
5,276,166 A *  1/1994  Swarup et al. ............. 548/952

FOREIGN PATENT DOCUMENTS

| DE | 1258604 | 1/1968 |
|---|---|---|
| DE | 3627246 | 2/1988 |
| DE | 4021659 | 1/1992 |
| EP | 858038  | 1/1961 |

OTHER PUBLICATIONS http://www2.volstate.edu/chem/2010/Labs/Cyclohexene.html (Nov. 27, 2005).*
Marinetti, Angela et al.; "Enantioselective preparation of 2,4-disubstituted azetidines"; Chemical Abstracts Service, Columbus, Ohio, XP002319678 gefunden im STN database accession No. 2000:336170, 2 pgs.
Testa, I. Emilio et al.; "Substances acting on the central nervous system. XIV. 3,3-Disubstituted azetidines"; Chemical Abstracts Service, Columbus, Ohio, XP002319679 gefunden im STN database accession No. 1962:45914, 6 pgs.
Murakami, Masuo et al.; "Diazoniadispiroalkane salts"; Chemical Abstracts Service, Columbus, Ohio, XP002319680 gefunden im STN database accession No. 1970:111531, 2 pgs.
Lunak, Stanislav et al.; "Hardenable epoxy compositions with increased storage stability"; Chemical Abstracts Service, Columbus, Ohio, XP002319681 gefunden im STN database accession No. 1986:554121, 2 pgs.

* cited by examiner

*Primary Examiner*—James Seidleck
*Assistant Examiner*—Gregory Listvoyb
(74) *Attorney, Agent, or Firm*—Fitch, Even, Tabin & Flannery

(57) ABSTRACT

A description is given of azetidine derivatives and methods for producing them, and of their use as a latent curing component for resins having functional groups which are reactive toward amino groups. The particular advantages of the curing component proposed in accordance with the invention, such as effective producibility, high environmental friendliness, and excellent storage stability of the resin/curing agent mixtures, make these azetidine derivatives outstandingly suitable for one-component, moisture-hardening polymer compositions, which are of special interest in particular for the production of (floor) coatings, sealants, and adhesives.

3 Claims, No Drawings

AZETIDINE DERIVATIVES, METHOD FOR PRODUCING SAID DERIVATIVES AND USE THEREOF

The present invention relates to azetidine derivatives, to methods for producing them, and to their use as a latent curing component for resins having functional groups which are reactive toward amines, especially polyurethane resins and polyepoxide resins.

Latent curing components are used in particular for moisture-curing polyurethane compositions in the production of sealants, adhesives, and coating materials. In the prior art a whole series of latent curing agents have already been described, but they all have the serious disadvantage that the curing reaction is accompanied by release of volatile organic compounds which either pollute the environment and/or appear problematic from a health standpoint.

For instance, DE-A 30 19 356 describes, as curing agents for polyisocyanates, compounds which contain aldimine groups and oxazolidine groups and are prepared by a) reacting polyamines with an epoxide compound and b) subsequently cyclizing the polyamino alcohols, formed in stage a), with aldehydes. When these aldiminooxazolidines are cured with polyisocyanates, in the presence of water or atmospheric moisture, aldehydes are eliminated which in some circumstances represent a severe odor nuisance and can therefore be used only in the outdoor sector.

DE-A 36 24 924 discloses moisture-curing, storage-stable, one-component polyurethane systems which in addition to the polyurethane prepolymer include, as a component essential to the invention, a polyaldimine as curing agent. With these polyurethane systems as well, aldehydes are eliminated in the course of curing, and so use for the interior sector is ruled out from the outset. A further disadvantage associated with these polyurethane systems is the fact that the corresponding polyurethane prepolymers have a relatively high viscosity, so that diethyl malonates must be added in order to reduce the viscosity.

In accordance with DE-A 40 21 659, bisoxazolanes are recommended as curing agents for polyurethane systems, and are prepared by reacting diethanolamine with aldehydes. Although solvent-free products of low viscosity can be provided in this way, these bisoxazolanes give off two moles of aldehyde per mole of curing agent in the course of the curing reaction, and such elimination is associated with the disadvantages already described above.

Moreover, in EP-A 291 850, one-component polyurethane systems are described which in addition to the polyurethane prepolymer include a latent curing agent from the group consisting of oxazolidines, enamines, and azomethines, preferably ketimines and/or aldimines. These compounds too give off unwanted aldehydes or ketones in the course of hydrolysis in the presence of moisture. Furthermore, in order to reduce the increase in viscosity, diethyl malonates must be added to the polyurethane prepolymers or one-component polyurethane systems, in an amount of up to 10% by weight.

WO 95/11 933 discloses aldimine-oxazolidines. Apart from the relatively complicated preparation, the release of aldehydes in the course of the curing reaction of these compounds must be regarded as particularly disadvantageous.

EP-A 947 529, finally, discloses polyurethane prepolymers which in addition to the isocyanate groups contain latent amino groups. These polyurethane prepolymers are prepared by addition reaction of an amino-aldimine or of a cycloaminal with the isocyanate group of a polyurethane polymer. With this polyurethane system as well the elimination of benzaldehyde in the course of the curing reaction assisted by water or atmospheric moisture is unavoidable.

The object on which the present invention was based, therefore, was to provide a latent curing component for resins containing amine-reactive functional groups that does not have the stated disadvantages of the prior art but instead does not eliminate any volatile organic compounds in the course of moisture-induced curing, possesses good performance properties, and can be prepared relatively easily and inexpensively.

This object has been achieved in accordance with the invention through azetidine derivatives of the general formula (I) according to claim 1.

It has surprisingly emerged that, with the curing component provided in accordance with the invention, no organic compounds at all are eliminated in the course of the curing reaction. Furthermore, the latent curing agents of the invention can be formulated effectively with all common isocyanate-functional and/or epoxy-functional systems, with the corresponding curing agent/resin reaction products exhibiting very good storage stability over a relatively long time period, which likewise was not foreseeable.

In accordance with the invention, as a latent curing component, an azetidine derivative of the general formula (I) is provided

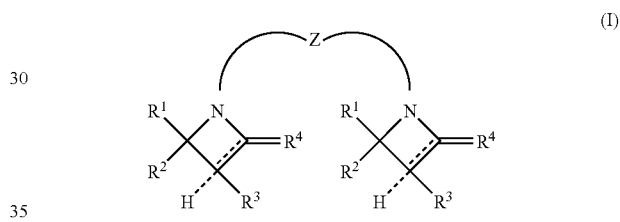

where
$R^1$, $R^2$ and $R^3$ independently of one another are H, $C_1$-$C_{20}$ alkyl, $C_3$-$C_8$ cycloalkyl, $C_6$-$C_{10}$ aryl or alkylaryl with $C_1$-$C_4$ alkyl and $C_6$-$C_{10}$ aryl groups
$Z=C_2$-$C_{25}$ alkylidene, $C_5$-$C_{25}$ cycloalkylidene, $C_6$-$C_{24}$ arylene and also

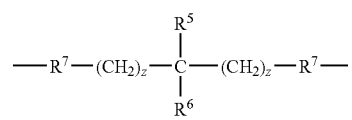

$R^5$ and $R^6$=H, $CH_2OH$, $C_1$-$C_4$ alkyl, $C_6H_5$,

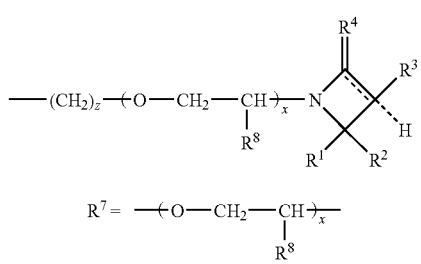

$R^8$=H, $CH_3$, $C_2H_5$, $C_6H_5$
$z=0$ or $1$
$x=0$ to $100$.

Preferred alkyl radicals, which may be either linear or branched, are $C_1$ to $C_4$ alkyl groups. With regard to the cycloalkyl radicals, cyclopentyl and cyclohexyl groups, and with regard to the aryl radicals, phenyl and naphthyl groups, are regarded as being preferred.

One preferred embodiment uses, in particular, azetidine derivatives of the general formula (II)

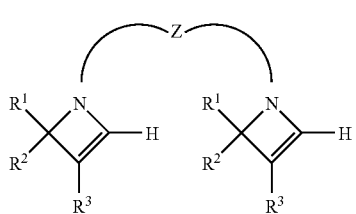

(II)

where $R^1$, $R^2$, $R^3$, and Z are as defined above. The azetidine derivatives of the formula (II) are very easily preparable by reaction of one mole of the polyamine of the formula $H_2N$—$Z'$—$NH_2$ with two moles of an α,β-unsaturated aldehyde of the formula $R^1R^2$—C=$CR^3$CHO in accordance with equation (A), the cyclization to the bis-azetidine derivative taking place with elimination of water:

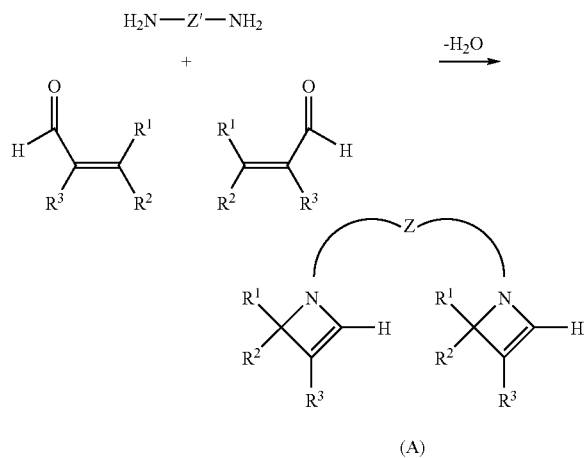

(A)

Z' here has the following definition:

$C_2$-$C_{25}$ alkylidene, $C_5$-$C_{25}$ cycloalkylidene, $C_6$-$C_{24}$ arylene, and

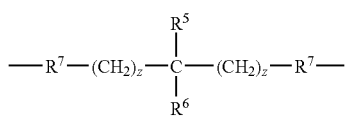

$R^5$ and $R^6$=H, $CH_2OH$, $C_1$-$C_4$ alkyl, $C_6H_5$,

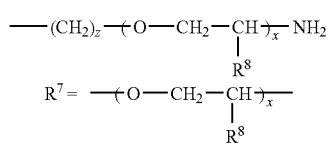

$R^8$=H, $CH_3$, $C_2H_5$, $C_6H_5$ z=0 or 1 x=0 to 100

Where the polyamine $NH_2$—$Z'$—$NH_2$ has three or four $NH_2$ groups, the corresponding tris- or tetrakis-azetidines can be prepared by reaction with three or four moles of the α,β-unsaturated aldehyde.

The reaction of one mole of the polyamine $H_2N$—$Z'$—$NH_2$ with two moles of an α,β-unsaturated ketone of the formula $R^1R^2C$=C—$CR^3$—$COR^4$ in accordance with equation (B) produces bis-azetidine derivatives of the general formula (III):

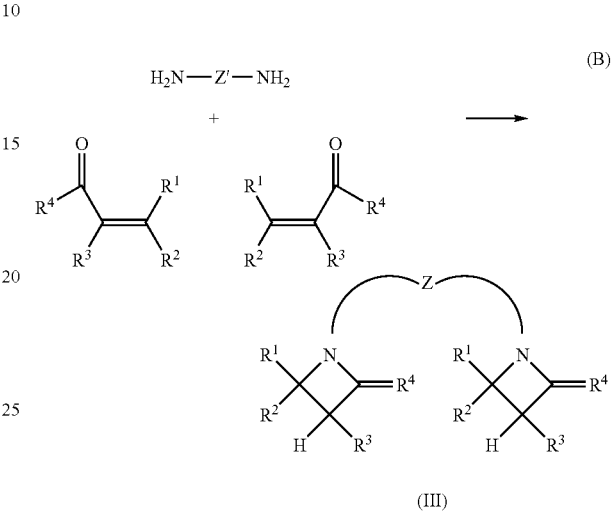

(III)

In the context of the present invention it is also possible for the polyamine $NH_2$—$Z'$—$NH_2$ to have three or four $NH_2$ groups. In these cases the corresponding tris- or tetrakis-azetidines are obtained by reaction of 1 mole of the polyamine with three or four moles of the α,β-unsaturated ketone $R^1R^2C$=$CR^3$—$COR^4$.

The production of the azetidine derivatives of the invention is relatively unproblematic and can take place by reaction of the polyamine with the α,β-unsaturated aldehyde or ketone in the presence of an organic solvent, especially toluene, in the temperature range from 20 to 150° C., in particular with removal of water.

The diazepine derivatives provided in accordance with the invention are outstandingly suitable as a latent curing component for resins having functional groups which are reactive toward amines. Latent curing components bring about moisture-induced curing.

The diazepine derivatives of the invention are preferably used for curing polyurethane resins and/or epoxy resins.

In the context of the present invention, however, it is readily possible to use the diazepine derivatives in association with other polymer systems, such as polyacrylates, for example, or with other polymer compounds which contain at least one amine-reactive group. In one preferred embodiment in this context the diazepine derivative of the formula I undergoes addition reaction, via the secondary amine, with the resin to be cured. On exposure to moisture the azetidine ring is then opened hydrolytically and the secondary amine which results in this case is able, finally, to react with the reactive functional groups of the resin to be cured.

This curing of the mixture composed of curing component and resin takes place preferably in the temperature range from 5 to 80° C., in particular at 10 to 60° C.

The amount of the curing component used is relatively uncritical, although on economic grounds it has proven particularly advantageous to use the azetidine derivative proposed in accordance with the invention in an amount of 0.01% to 150% by weight, in particular 0.1% to 20% by weight, based on the amount of the resin to be cured.

In view of the particular advantages of the curing component of the invention, such as effective producibility, high environmental friendliness (no volatile compounds are eliminated in the course of curing), and good storage stability of the resin/curing agent mixtures, azetidine derivatives of formulae (I) to (III) are outstandingly suitable for one-component, moisture-hardening polymer compositions, which are of special interest in particular for the production of sealants, adhesives, and coating materials, especially floor coating materials.

The examples below are intended to illustrate the invention in more detail.

EXAMPLES

All examples were produced with air exclusion in a nitrogen atmosphere.

Example 1 A

Preparation of a Bis-Azetidine Based on Jeffamin D-230

In a reaction vessel with water separator 30 g (0.306 mol) of mesityl oxide, 33.48 g (0.146 mol) of Jeffamin D-230 (Huntsman), and 0.1 g of p-toluenesulfonic acid are dissolved in 150 g of absolute toluene and the solution is heated to boiling. The reaction mixture is held at boiling temperature until water can no longer be removed via the water separator (theoretical: 5.24 g of water). Subsequently the toluene is removed completely. This gives a slightly orange-colored, oily product.

Example 1 B

Production of an NCO-Containing Prepolymer with the Bisazetidine Curing Agent Derivative from Example 1A In a reaction vessel 250 g (0.125 mol) of polypropylene glycol Dow Voranol P2000 (from Dow) are held with 55.55 g (0.25 mol) of isophorone diisocyanate and 0.1 g of T12-DBTL at 85° C. until the theoretical NCO content of 3.44% by weight is reached.

Subsequently 48.0 g (0.123 mol) of bisazetidine derivative from Example 1A are stirred into 300.0 g of the NCO-containing prepolymer at room temperature.

The product obtained is resinous, is transparently clear, and possesses a weak orange coloration. Drawn down on a glass plate, it cures right through within a short time without any unpleasant odor nuisance. Even in a high-build application, curing takes place right through.

Example 1 C

Production of an NCO-Containing Prepolymer with the Bisazetidine Curing Agent Derivative from Example 1A In a reaction vessel 250 g (0.125 mol) of polypropylene glycol Dow Voranol P2000 (from Dow) are held with 43.54 g (0.25 mol) of toluene diisocyanate and 0.1 g of T12-DBTL at 85° C. until the theoretical NCO content of 3.58% by weight is reached.

Subsequently 40.0 g (0.102 mol) of bisazetidine derivative from Example 1A are stirred into 250.0 g of the NCO-containing prepolymer at room temperature.

The product obtained is resinous, is transparently clear, and possesses a weak orange coloration. Drawn down on a glass plate, it cures right through without any unpleasant odor nuisance. Even in a high-build application, curing takes place right through.

Example 2 A

Preparation of a Bis-Azetidine Based on 1,6-hexamethylenediamine

In a reaction vessel with water separator 30 g (0.306 mol) of mesityl oxide, 16.91 g (0.146 mol) of 1,6-hexamethylenediamine, and 0.1 g of p-toluenesulfonic acid are dissolved in 150 g of absolute toluene and the solution is heated to boiling. The reaction mixture is held at boiling temperature until water can no longer be removed via the water separator (theoretical: 5.24 g of water). Subsequently the toluene is removed completely.

Example 2 B

Production of an NCO-Containing Prepolymer with the Bisazetidine Curing Agent Derivative from Example 2A In a reaction vessel 250 g (0.125 mol) of polypropylene glycol Dow Voranol P2000 (from Dow) are held with 42.05 g (0.25 mol) of hexamethylene 1,6-diisocyanate and 0.1 g of T12-DBTL at 85° C. until the theoretical NCO content of 3.60% by weight is reached.

Subsequently 28.33 g (0.102 mol) of bisazetidine derivative from Example 2A are stirred into 250 g of the NCO-containing prepolymer at room temperature.

The product obtained is resinous, is transparently clear, and possesses a weak yellowish coloration. Drawn down on a glass plate, it cures right through without any unpleasant odor nuisance. Even in a high-build application, curing takes place right through.

Example 2 C

Production of an NCO-Containing Prepolymer with the Bisazetidine Curing Agent Derivative from Example 2A In a reaction vessel 250 g (0.125 mol) of polypropylene glycol Dow Voranol P2000 (from Dow) are held with 65.59 g (0.25 mol) of H12MDI and 0.1 g of T12-DBTL at 85° C. until the theoretical NCO content of 3.33% by weight is reached.

Subsequently 35.78 g (0.129 mol) of bisazetidine derivative from Example 2A are stirred into the NCO-containing prepolymer at room temperature.

The product obtained is resinous, is transparently clear, and possesses a weak yellowish coloration. Drawn down on a glass plate, it cures right through without any unpleasant odor nuisance. Even in a high-build application, curing takes place right through.

Example 2 D

Formulation of an Epoxy-Functional Resin with the Bisazetidine Curing Agent Derivative from Example 2A At 40° C. 203.2 g (0.735 mol) of bisazetidine derivative from Example 2A are stirred homogeneously into 250 g (0.735 mol) of bisphenol A diglycidyl ether.

The product obtained is viscous, is transparently clear, and possesses a weak yellowish coloration. Drawn down on a glass plate, it cures right through without any unpleasant odor nuisance.

Example 3 A

Preparation of a Tris-Azetidine Based on Jeffamin T-403

In a reaction vessel with water separator 30 g (0.306 mol) of mesityl oxide, 45.85 g (0.102 mol) of Jeffamin T-403 (Huntsman), and 0.1 g of p-toluene-sulfonic acid are dissolved in 150 g of absolute toluene and the solution is heated to boiling. The reaction mixture is held at boiling temperature until water can no longer be removed via the water separator (theoretical: 5.50 g of water). Subsequently the toluene is removed completely. This gives a slightly orange-colored, resinous oil.

Example 3 B

Production of an NCO-Containing Prepolymer with the Trisazetidine Curing Agent Derivative from Example 3A In a reaction vessel 250 g (0.125 mol) of polypropylene glycol Dow Voranol P2000 (from Dow) are held with 42.05 g (0.25 mol) of hexamethylene 1,6-diisocyanate and 0.1 g of T12-DBTL at 85° C. until the theoretical NCO content of 3.60% by weight is reached.

Subsequently 57.66 g (0.0835 mol) of trisazetidine derivative from Example 3A are stirred into the NCO-containing prepolymer at room temperature.

The product obtained is resinous, is transparently clear, and possesses a weak orange coloration. Drawn down on a glass plate, it cures right through without any unpleasant odor nuisance. Even in a high-build application, curing takes place right through.

Example 3 C

Formulation of an Epoxy-Functional Resin with the Trisazetidine Curing Agent Derivative from Example 3A At 40° C. 338.26 g (0.490 mol) of trisazetidine derivative from Example 3A are stirred homogeneously into 250 g (0.735 mol) of bisphenol A diglycidyl ether. The product obtained is viscous, is transparently clear, and possesses a weak yellowish coloration. Drawn down on a glass plate, it cures right through without any unpleasant odor nuisance.

Example 4 A

Preparation of a Tris-Azetidine Based on Jeffamin T-403

In a reaction vessel with water separator 30 g (0.357 mol) of 3-methylcrotonaldehyde, 53.50 g (0.119 mol) of Jeffamin T-403 (Huntsman), and 0.1 g of p-toluenesulfonic acid are dissolved in 200 g of absolute toluene and the solution is heated to boiling. The reaction mixture is held at boiling temperature until water can no longer be removed via the water separator (theoretical: 6.42 g of water). Subsequently the toluene is removed completely. This gives a slightly orange-colored, resinous oil.

Example 4 B

Production of an NCO-Containing Prepolymer with the Trisazetidine Curing Agent Derivative from Example 4A In a reaction vessel 250 g (0.125 mol) of polypropylene glycol Dow Voranol P3000 (from Dow) are held with 28.03 g (0.167 mol) of hexamethylene 1,6-diisocyanate and 0.1 g of T12-DBTL at 85° C. until the theoretical NCO content of 2.52% by weight is reached.

Subsequently 36.03 g (0.0556 mol) of trisazetidine derivative from Example 4A are stirred into the NCO-containing prepolymer at room temperature.

The product obtained is resinous, is transparently clear, and possesses a weak orange coloration. Drawn down on a glass plate, it cures right through without any unpleasant odor nuisance. Even in a high-build application, curing takes place right through.

Example 5 A

Preparation of a Bis-Azetidine Based on Jeffamin D-230

In a reaction vessel with water separator 30 g (0.357 mol) of 3-methylcrotonaldehyde, 41.00 g (0.178 mol) of Jeffamin D-230 (Huntsman), and 0.1 g of p-toluenesulfonic acid are dissolved in 150 g of absolute toluene and the solution is heated to boiling. The reaction mixture is held at boiling temperature until water can no longer be removed via the water separator (theoretical: 6.42 g of water). Subsequently the toluene is removed completely. This gives a slightly orange-colored oil.

Example 5 B

Formulation of an Epoxy-Functional Resin with the Bisazetidine Curing Agent Derivative from Example 5A At 40° C. 266.25 g (0.735 mol) of bisazetidine derivative from Example 5A are stirred homogeneously into 250 g (0.735 mol) of bisphenol A diglycidyl ether.

The product obtained is viscous, is transparently clear, and possesses a weak yellowish coloration. Drawn down on a glass plate, it cures right through without any unpleasant odor nuisance.

Example 6

Storage Stability Test

The mixtures of prepolymers and latent curing agents produced in accordance with Examples 1 to 5 are subjected to storage in closed vessels at room temperature (20-25° C.), the results obtained being as follows:

After a storage time of 12 months at a temperature between 20-25° C. in lightfast and airtight vessels, no notable change in color was found for any of the examples. The increase in viscosity over this period was very low (increase by a factor in the range of 1.1-1.3 relative to the initial viscosity) and exhibited no effect at all on the curing or the processing properties.

The invention claimed is:

1. An azetidine derivative of the general formula (II) or (III)

formula (II) or (III)

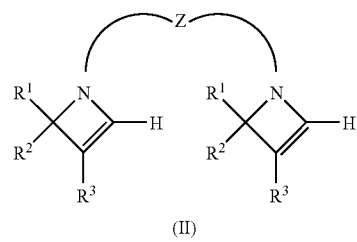

(II)

-continued

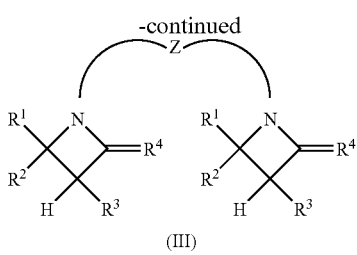
(III)

where
$R^1$, $R^2$ and $R^3$ independently of one another are H, $C_1$-$C_{20}$ alkyl, $C_3$-$C_8$ cycloalkyl, $C_6$-$C_{10}$ aryl or alkylaryl with $C_1$-$C_4$ alkyl and $C_6$-$C_{10}$ aryl groups
$R^4$=H, or $C_1$-$C_6$ alkyl (idene)
Z=$C_2$-$C_{25}$ alkylidene, $C_5$-$C_{25}$ cycloalkylidene, $C_6$-$C_{24}$ arylene or

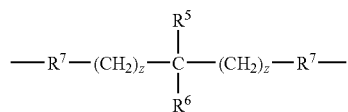

$R^5$ and $R^6$=H, $CH_2OH$, $C_1$-$C_4$ alkyl, $C_6H_5$ or

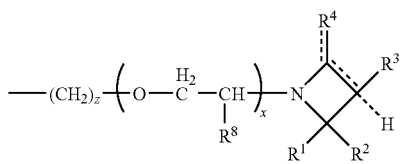

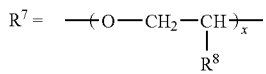

$R^8$=H, $CH_3$, $C_2H_5$ or $C_6H_5$
z=0 or 1
x=0 to 100.

2. A method for producing an azetidine derivative of claim 1, wherein a polyamine of the formula $NH_2$—Z'—$NH_2$ is reacted with an α,β-unsaturated aldehyde of the formula $R^1R^2$—C=$CR^3$CHO or with an α,β-unsaturated ketone of the formula $R^1R^2C$=$CR^3$—$COR^4$ in the temperature range from 20 to 150° C., where Z' is
$C_2$-$C_{25}$ alkylidene, $C_5$-$C_{25}$ cycloalkylidene, $C_6$-$C_{24}$ arylene, or

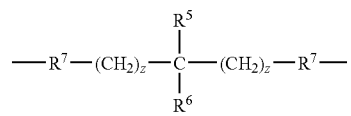

$R^5$ and $R^6$=H, $CH_2OH$, $C_1$-$C_4$ alkyl, $C_6$, $H_5$, or

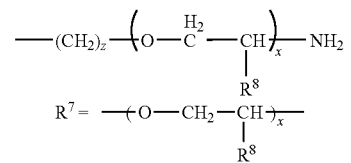

$R^8$=H, $CH_3$, $C_2H_5$, or $C_6H_5$
z=0 or 1
x=0 to 100
$R^1$, $R^2$ and $R^3$ independently of one another are H, $C_1$-$C_{20}$ alkyl, $C_3$-$C_8$ cycloalkyl, $C_6$-$C_{10}$ aryl or alkylaryl with $C_1$-$C_4$ alkyl and $C_6$-$C_{10}$ aryl groups;
$R^4$=H, or $C_1$-$C_6$ alkyl (idene).

3. The method of claim 2, wherein the reaction is carried out in the presence of an organic solvent.

* * * * *